(12) United States Patent
Beckmann et al.

(10) Patent No.: US 7,708,690 B2
(45) Date of Patent: May 4, 2010

(54) PATIENT CARE UNIT WITH A BED

(75) Inventors: Udo Beckmann, Stockelsdorf (DE);
Henning Gerder, Lübeck (DE)

(73) Assignee: Dräger Medical AG & Co. KG, Lübeck (DE)

( * ) Notice: Subject to any disclaimer, the term of this patent is extended or adjusted under 35 U.S.C. 154(b) by 875 days.

(21) Appl. No.: 11/058,623

(22) Filed: Feb. 15, 2005

(65) Prior Publication Data
US 2005/0267339 A1    Dec. 1, 2005

(30) Foreign Application Priority Data
May 26, 2004    (DE)    ........................ 10 2004 025 797

(51) Int. Cl.
*A61B 5/00*    (2006.01)
(52) U.S. Cl. ...................... 600/300; 600/301
(58) Field of Classification Search ........................ None
See application file for complete search history.

(56) References Cited
U.S. PATENT DOCUMENTS 5,640,953 A * 6/1997 Bishop et al. ............... 600/300
5,664,270 A * 9/1997 Bell et al. ....................... 5/600
5,882,300 A * 3/1999 Malinouskas et al. ........ 600/300
6,352,503 B1 * 3/2002 Matsui et al. ................ 600/104
6,493,568 B1 * 12/2002 Bell et al. .................... 600/323
6,749,566 B2 * 6/2004 Russ ............................ 600/300
2002/0013517 A1 * 1/2002 West et al. .................... 600/300
2006/0015017 A1 * 1/2006 Cosentino et al. ........... 600/300

FOREIGN PATENT DOCUMENTS
WO        WO 98/34577        8/1998

* cited by examiner

*Primary Examiner*—Robert L Nasser
(74) *Attorney, Agent, or Firm*—McGlew and Tuttle, P.C.

(57) ABSTRACT

A patient care unit (1) with a bed for accommodating a patient makes possible undisturbed accessibility to the patient by avoiding cable connections between sensors at the patient and the measuring instruments or treating devices (2) belonging to them. The patient care unit (1) has a receiving unit for receiving sensor signals of the patient, transmission features for passing on the sensor signals to a transmitting unit in the patient care unit (1) or to a cable connection (4) for connecting the patient care unit (1) to the power supply, so that the sensor signals enter measuring instruments or treating devices (2) that belong to them for the evaluation of the sensor signals in a wireless manner or via the power supply.

21 Claims, 2 Drawing Sheets

US 7,708,690 B2

PATIENT CARE UNIT WITH A BED

CROSS REFERENCE TO RELATED APPLICATIONS

This application claims the benefit of priority under 35 U.S.C. §119 of German Patent Application DE 10 2004 025 797.3 filed May 26, 2004, the entire contents of which are incorporated herein by reference.

FIELD OF THE INVENTION

The present invention pertains to a patient care unit with a bed for accommodating a patient.

BACKGROUND OF THE INVENTION

During a medical treatment, for example, surgery or stay in an intensive care unit, it is necessary to use various measuring instruments in the vicinity of the patient for monitoring physiological vital parameters (measured variables) of the patient, who is located, in general, on a patient care unit with a bed, for example, on an operating (OP) table.

The measuring instruments receive sensor signals, the sensors being used are, for example, sensors for measuring the oxygen saturation or the oxygen concentration, as well as sensors for measuring the $CO_2$ concentration in the breathing air. Other sensor signals are generated by EKG electrodes. CCD (Charge Coupled Device) sensors are also used for image transmission to a monitor in minimally invasive surgery. The sensor signals are bound, in general, to lines, i.e., they are transmitted via electric lines to the particular measuring instruments, which are located, as a rule, outside the patient's direct area. The energy supply for the sensors is also provided mostly via electric lines, which are optionally integrated in a cable bundle.

A prior-art telemetry system for the transmission of EKG and sensor signals for the oxygen saturation of the blood has the drawback that a relatively high transmitting power must be selected in order to reliably make it possible to reach ranges of several meters. This may be associated with undesired physiological effects of electromagnetic fields on the body. In addition, the cable bundling and consequently the signal bundling of the individual sensors take place via a so-called "pod," a cable connector, which lies loosely in a disturbing manner. In addition, a cable must be laid from the pod to the measuring instrument or to the monitor. In general, a plurality of measuring instruments and/or treating devices must be additionally networked with one another via lines, so that, on the whole, a plurality of electric cables hinder undisturbed access to the patient.

SUMMARY OF THE INVENTION

Thus, the object of the present invention is to provide a patient care unit with a bed for receiving a patient, which makes possible undisturbed accessibility to the patient for the medical personnel and makes it possible to set up the measuring instruments or treating devices independently from the position of the sensors belonging to them at the patient.

According to the invention, a patient care unit is provided with a bed for accommodating a patient and with means for receiving sensor signals of the patient as well as means for passing on the sensor signals to a transmitting unit in the patient care unit or to a cable connection for connecting the patient care unit to the power supply. The sensor signals reach the corresponding measuring instruments or treating devices for evaluating the sensor signals in a wireless manner or via the power supply.

An essential advantage of the present invention is the use of the patient care unit directly as a connection unit for the sensors at the patient, who is located on the bed of the patient care unit, so that the laying of cables from the patient to the corresponding measuring instruments or treating devices is practically eliminated and the hygienic conditions can thus also be improved because no cables will lie around any longer in the area of the patient and on the floor.

The means for receiving sensor signals of the patient may comprise electric sensor connection lines and the terminals, which belong to them and can be preferably connected via plug type connections, or they have an inductive design.

The patient care unit or bed support may be provided with at least one receiving antenna for receiving sensor signals of the patient.

The sensor signals of the patient may be related to measured physiological variables, especially blood pressure, oxygen and/or $CO_2$ concentration in the blood, and electrode signals from said EKG electrodes.

Electric lines may be present for passing on the sensor signals into the patient care unit.

The patient care unit may be an operating table or a hospital bed. The treating device may be an anesthesia apparatus or a respirator.

Exemplary embodiments of the present invention will be described below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
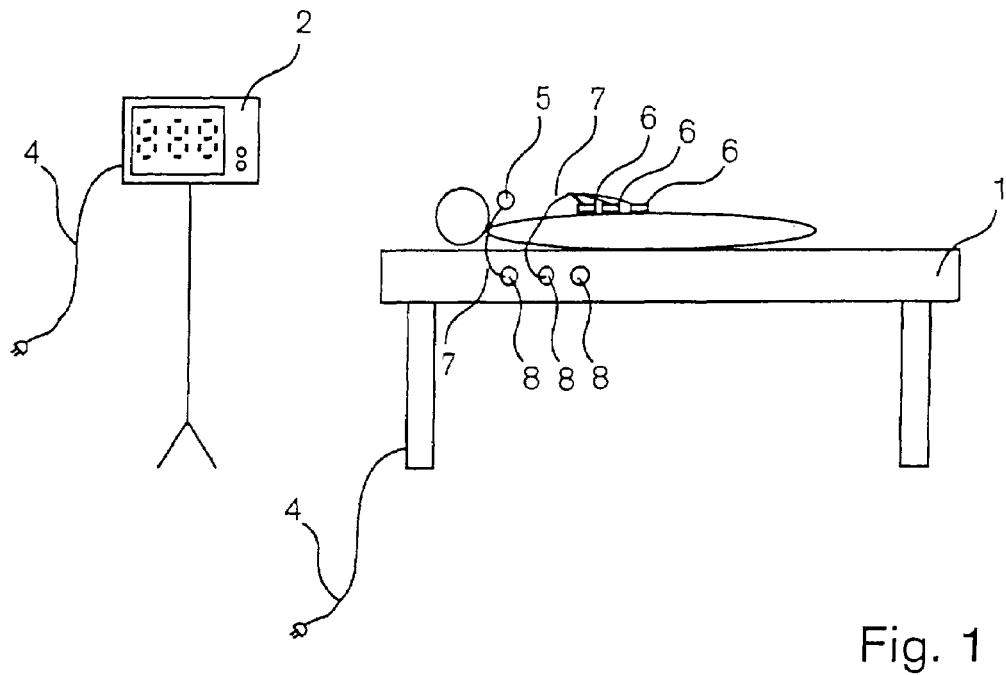
FIG. 1 is a schematic view of a patient care unit with a patient with sensors and a measuring instrument belonging to it.
Figure 2:
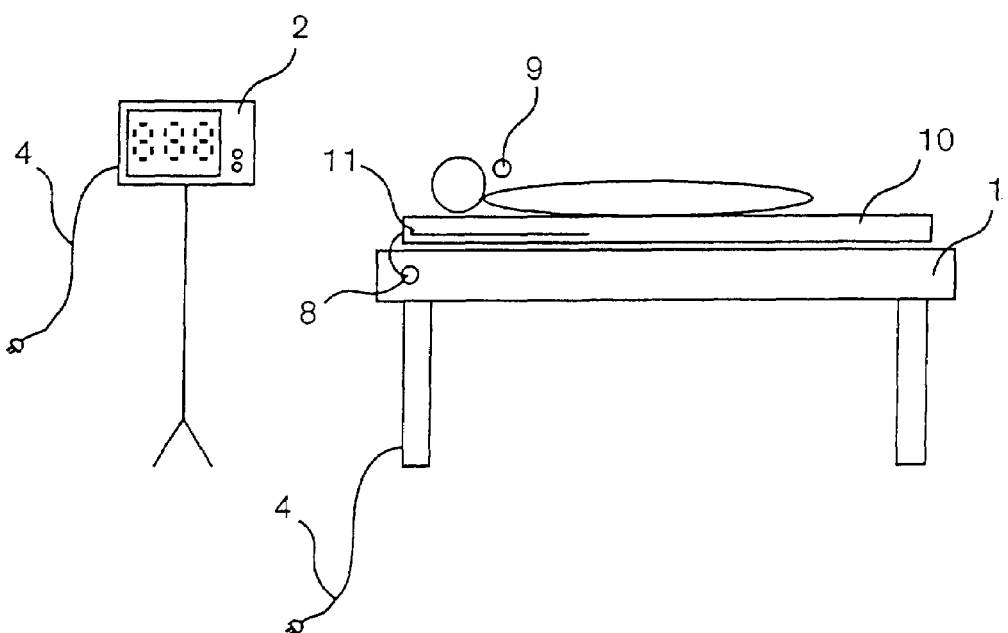
FIG. 2 is a schematic view of a patient care unit with a bed support with a receiving antenna.

Referring to the drawings in particular, the patient care unit 1 in FIGS. 1 and 2 is an operating (OP) table or a hospital bed, which is located, for example, in an intensive care unit of a hospital. The patient care unit 1 is connected via a cable connection 4 to the power supply with a usual a.c. voltage of 230 or 110 V, which is usually used for the electric adjustment of the table or bed. The measuring instruments 2 for the sensors are likewise connected to the power supply via at least one cable connection 4. The sensors used at the patient are, for example, a $CO_2$ sensor 5 or EKG electrodes 6 with sensor connection lines 7. The patient care unit 1 is used directly as a connection unit for the sensors and thus assumes the task of a cable concentrator. The connection to the patient care unit 1 is performed either via an electric contacting by means of the sensor connection lines 7 and the corresponding terminals 8 or inductively, for example, by means of a suction foot or suction foot plug. The analog sensor signals are preferably digitized directly in the sensor head in order to guarantee the interference-free transmission of the data. The sensors are likewise supplied with energy via the terminals 8 of the patient care unit 1. The optionally digitized sensor signals are passed on to the corresponding measuring instruments and/or optionally treating devices 2 preferably via the power supply. These measuring instruments and/or treating devices may be, in principle, any line-powered devices, such as operating tables, hospital beds, heating mattresses, anesthesia apparatus or respirators and monitoring devices. The signal or data connection via the power supply is still present even in vase of devices that are equipped with an emergency power supply or have a battery mode of operation for the case of a possible power failure. As an alternative, the signal transmission takes place in a wireless manner by means of radio (of a transmitting unit incorporated in the patient care unit 1) from the patient care unit 1 to the measuring instruments or treating devices 2.

According to FIG. 2, at least one receiving antenna 11 is integrated in the patient care unit 1 or in the bed support 10 in order to receive the sensor signals from the wireless, battery-operated sensors 9 and to subsequently forward them as described. Such battery-operated sensors 9 are, for example, temperature sensors, which are attached to the patient's body by means of adhesive elements, or $CO_2$ sensors. This embodiment has the advantage that the necessary transmission power of the sensors can be very low ($\mu$W), which minimizes the possible physiological action on the patient, because the transmission path to be bridged over up to the patient care unit 1 is only a few cm. An optional variant of this embodiment uses the so-called intrabody communication, in which the data are passed on via the patient's body, for the data transmission between the sensors and the collection point in the patient care unit 1.

Figure 3:
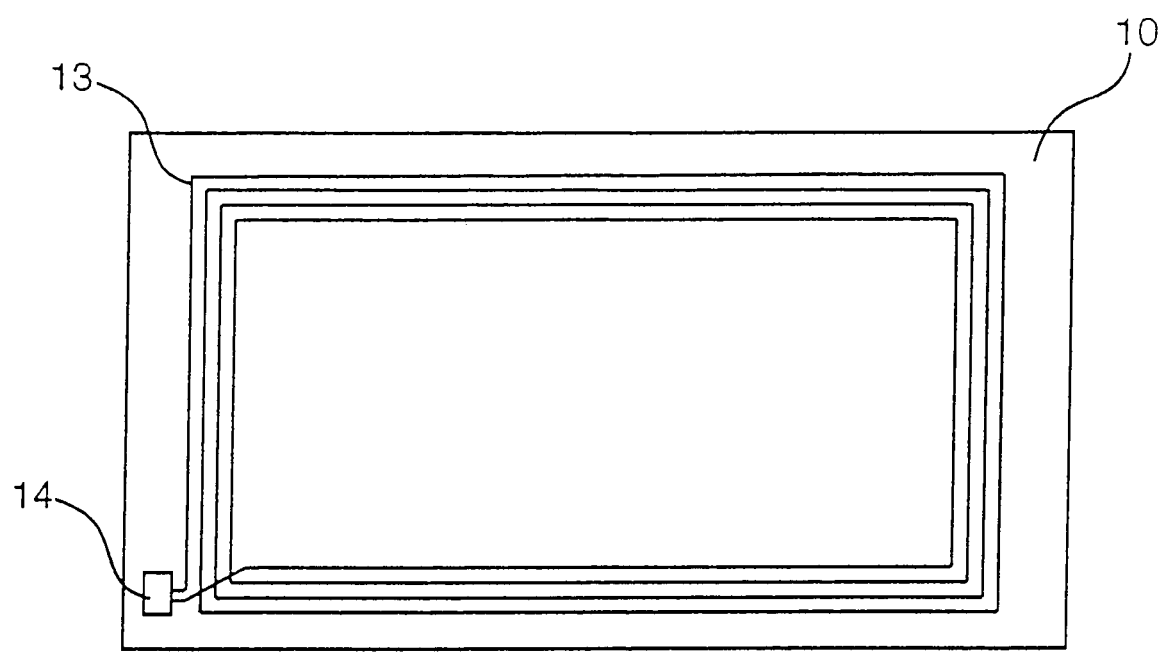
FIG. 3 is a top view of the bed of the patient care unit with an integrated inductance for receiving the sensor signals and an optional energy supply unit for the sensors.

The data transmission between a sensor at the patient and the patient care unit 1 may also be carried out inductively, by means of a coil, over a distance of a few cm, by integrating a large inductance 13 in the patient care unit 1 or in the bed support (FIG. 3). The actuating unit of the inductance 13 and the data digitization by means of a converter 14 is preferably integrated in the patient care unit 1. To minimize interferences from the environment, a directed reading cone is preferably used. At the same time, sensors with very low power consumption ($\mu$W) can be supplied with energy in this manner, corresponding to the transponder principle.

While specific embodiments of the invention have been shown and described in detail to illustrate the application of the principles of the invention, it will be understood that the invention may be embodied otherwise without departing from such principles.

What is claimed is:

1. A patient care unit with a bed for accommodating a patient, the patient care unit comprising:
    means for receiving sensor signals of the patient from sensors that are not a part of the patient care unit; and
    means non-detachably integrated to the patient care unit for passing on the sensor signals to a cable connection for connecting said patient care unit to a power supply, so that the sensor signals reach said corresponding measuring instruments or treating devices for evaluating the sensor signals via the power supply.

2. A patient care unit in accordance with claim 1, wherein the means for receiving sensor signals of the patient comprise electric sensor connection lines and terminals associated therewith.

3. A patient care unit in accordance with claim 2, wherein said electric sensor connection lines and terminals are connected via plug type connections, or have an inductive coupling.

4. A patient care unit in accordance with claim 1, wherein the patient care unit or a bed support is provided with a receiving antenna for receiving sensor signals of the patient.

5. A patient care unit in accordance with claim 1, wherein the sensor signals of the patient are related to measured physiological variables, especially blood pressure, oxygen and/or $CO_2$ concentration in the blood, and electrode signals from EKG electrodes.

6. A patient care unit in accordance with claim 1, wherein electric lines are present for passing on the sensor signals into the patient care unit.

7. A patient care unit in accordance with claim 1, wherein the patient care unit is an operating table or a hospital bed.

8. A patient care unit in accordance with claim 1, wherein the treating device is an anesthesia apparatus or a respirator.

9. A patient care unit system, comprising:
    a measuring instrument or treating device;
    a patient care unit bed for accommodating a patient, said patient care unit bed including support structure and a bed surface, said support structure for supporting said bed surface;
    a plurality of sensors operatively positioned relative to the patient with each of said sensors generating sensor signals;
    a concentrator including terminals, said sensors being operatively connected to said patient care unit bed via said terminals for receiving sensor signals of the patient at said patient care unit bed, said terminals being fixed to said patient care unit bed with said cable concentrator permanently integrated into and fixed to said patient care unit support structure for movement with said support structure;
    a cable connection fixed to said patient care unit bed support structure for movement with said support structure, said cable connection including a power supply connector for connecting said concentrator to a power supply, said cable connection being connected to said cable concentrator for supplying power to said terminals; and
    transmission means permanently fixed within said patient care unit bed for movement with said support structure, said transmission means including a transmitter and receiver connected to said cable connection for passing on the sensor signals from said cable concentrator to said measuring instrument or treating device via said cable connection power supply connector, so that said sensor signals reach said corresponding measuring instruments or treating devices for evaluating the sensor signals via said cable connection and said power supply.

10. A system in accordance with claim 9, wherein said connection of said sensors to said cable concentrator is by connection lines connected to one or more of said sensors and connected with one or more of said terminals, via plug type connections, or via a wireless transmitter connected to one or more of said sensors and an antenna connected to one or more terminals of said cable concentrator or via a communication device connected to one or more of said sensors and a communications device connected to one or more of said terminals of an inductive design.

11. A system in accordance with claim 9, wherein the system or a bed support is provided with a receiving antenna for receiving sensor signals of the patient, said receiving antenna being connected to one of said terminals.

12. A system in accordance with claim 9, wherein the sensor signals of the patient are related to measured physiological variables, especially blood pressure, oxygen and/or $CO_2$ concentration in the blood, and electrode signals from EKG electrodes.

13. A system in accordance with claim 9, wherein the system is an operating table or a hospital bed.

14. A system in accordance with claim 9, wherein the treating device is an anesthesia apparatus or a respirator.

15. A patient care unit system comprising:
- one or more measuring instruments or treating devices connected to a power source via a power cable for providing power to said one or more measuring instruments or treating devices, said one or more measuring instruments or treating devices each including at least a power transceiver for sending and receiving signals over said power line via said power source;
- a patient care unit including a bed with bed surface for accommodating a patient and a bed support structure supporting said bed with bed surface;
- a concentrator integrated into and fixed in said bed support structure, said concentrator including terminals;
- a power supply cable integrated into and fixed in said bed support structure, said power supply cable providing power to the patient care unit and to said cable concentrator;
- a plurality of sensors operatively positioned relative to the patient with each of said sensors generating sensor signals for said one or more measuring instruments or treating devices;
- an operative connection from each of said sensors to one of said terminals; and
- a transmission means non-detachably connected within said patient care unit including a transceiver for passing on the sensor signals from said cable concentrator terminals along said power supply cable to said measuring instruments or treating devices via said power supply for evaluating and/or displaying information provided from or derived from said sensor signals.

16. A system in accordance with claim 15, wherein said operative connection from one of said sensors to one of said terminals comprises a power and communications cable providing said one of said sensors with power via said one of said terminals and transmitting said sensor signals from said one of said sensors to said one of said terminals.

17. A system in accordance with claim 15, further comprising an antenna connected to one of said terminals wherein said operative connection from at least one of said sensors to one of said terminals comprises a wireless transmitter at said one of said sensors transmitting said sensors signals from said at least one of said sensors to said antenna connected to said one of said terminals.

18. A system in accordance with claim 15, wherein the sensor signals of the patient are related to measured physiological variables including one of blood pressure, oxygen and/or $CO_2$ concentration in the blood, and electrode signals from EKG electrodes wherein said one or more measuring instruments or treating devices comprise an anesthesia apparatus or a respirator.

19. A system in accordance with claim 15, wherein the patient care unit is one of a hospital bed and an operating table with electric adjustment means connected to said power supply cable for adjusting a position of said bed surface.

20. A system in accordance with claim 15, further comprising an inductance integrated into said patient care unit and connected to one of said terminals, at least one of said sensors including a transponder coil for receiving signals and power from said inductance and transmitting said sensor signals from said at least one of said sensors to said inductance.

21. A system in accordance with claim 15, further comprising an inductance integrated into said patient care unit and connected to one of said terminals, at least one of said sensors including a coil for transmitting said sensor signals from said at least one of said sensors to said inductance, said at least one of said sensors including a battery for powering said at least one of said sensors.

* * * * *